US00PP34038P2

(12) United States Plant Patent
Kievit et al.

(10) Patent No.: US PP34,038 P2
(45) Date of Patent: Mar. 15, 2022

(54) ***HEUCHERA* PLANT NAMED 'CARNIVAL BURGUNDY BLAST'**

(50) Latin Name: ***Heuchera* x *hybrida***
Varietal Denomination: Carnival Burgundy Blast

(71) Applicant: Ball Horticultural Company, West Chicago, IL (US)

(72) Inventors: Christa Kievit, Hem (NL); Karl F. Batschke, Geneva, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 17/460,260

(22) Filed: Aug. 29, 2021

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./440
CPC ... A01H 5/12; A01H 5/00; A01H 5/02; A01H 6/80; A01H 1/107; A01H 1/121
See application file for complete search history.

*Primary Examiner* — June Hwu
(74) *Attorney, Agent, or Firm* — Audrey Charles

(57) ABSTRACT

A new and distinct cultivar of *Heuchera* plant named 'Carnival Burgundy Blast', characterized by its dark burgundy colored foliage, and moderately vigorous, mounded growth habit, is disclosed.

1 Drawing Sheet

Latin name of genus and species of plant claimed: *Heuchera* x *hybrida.*

Variety denomination: 'Carnival Burgundy Blast'.

BACKGROUND OF THE INVENTION

The present invention relates to a new and distinct cultivar of *Heuchera* plant botanically known as *Heuchera* x *hybrida* and hereinafter referred to by the cultivar name 'Carnival Burgundy Blast'.

The new cultivar originated in a controlled breeding program in Hem, The Netherlands during the summer of 2016. The objective of the breeding program was the development of *Heuchera* cultivars with heat tolerance, unique foliage coloration and a mounded growth habit.

The new *Heuchera* cultivar is the result of open-pollination. The female (seed) parent of the new cultivar is 'Carnival Black Olive', not patented, characterized by its dark green and dark burgundy colored foliage, and moderately vigorous, compact-mounded growth habit. The male (pollen) parent of the new cultivar is unknown. The new cultivar was selected as a single flowering plant within the progeny of the above stated open-pollination during May 2017 in a controlled environment in Hem, The Netherlands.

Asexual reproduction of the new cultivar by in vitro propagation since May 2017 in Tenjo, Colombia and Bremen, Germany has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Carnival Burgundy Blast' as a new and distinct cultivar of *Heuchera* plant:

1. Dark burgundy and dark green colored foliage having a purple-grey colored overlay; and
2. Moderately vigorous, mounded growth habit. Plants of the new cultivar differ from plants of the female parent primarily in having more deeply lobed foliage with a purple-grey colored overlay. In addition the dark green foliage color is less pronounced than in the female parent.

Of the many commercially available *Heuchera* cultivars, the most similar in comparison to the new cultivar is 'Carnival Peach Parfait', U.S. Plant Pat. No. 24,928. However, in comparison, plants of the new cultivar differ from plants of 'Carnival Peach Parfait' in at least the following characteristics:

1. Plants of the new cultivar have a foliage that is darker burgundy colored than plants of 'Carnival Peach Parfait';
2. Plants of the new cultivar have a foliage apex that is minutely apiculate and not broadly acute like plants of 'Carnival Peach Parfait'; and
3. Plants of the new cultivar do not flower readily under standard outdoor growing conditions unlike plants of 'Carnival Peach Parfait'.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs differ slightly from the color values cited in the detailed description, which accurately describes the colors of 'Carnival Burgundy Blast'. The plants were approximately nine-months old. The plants were grown for approximately 15 weeks in 1.7 gallon containers in an outdoor shade nursery in West Chicago, Ill.

DETAILED BOTANICAL DESCRIPTION

Figure 1:
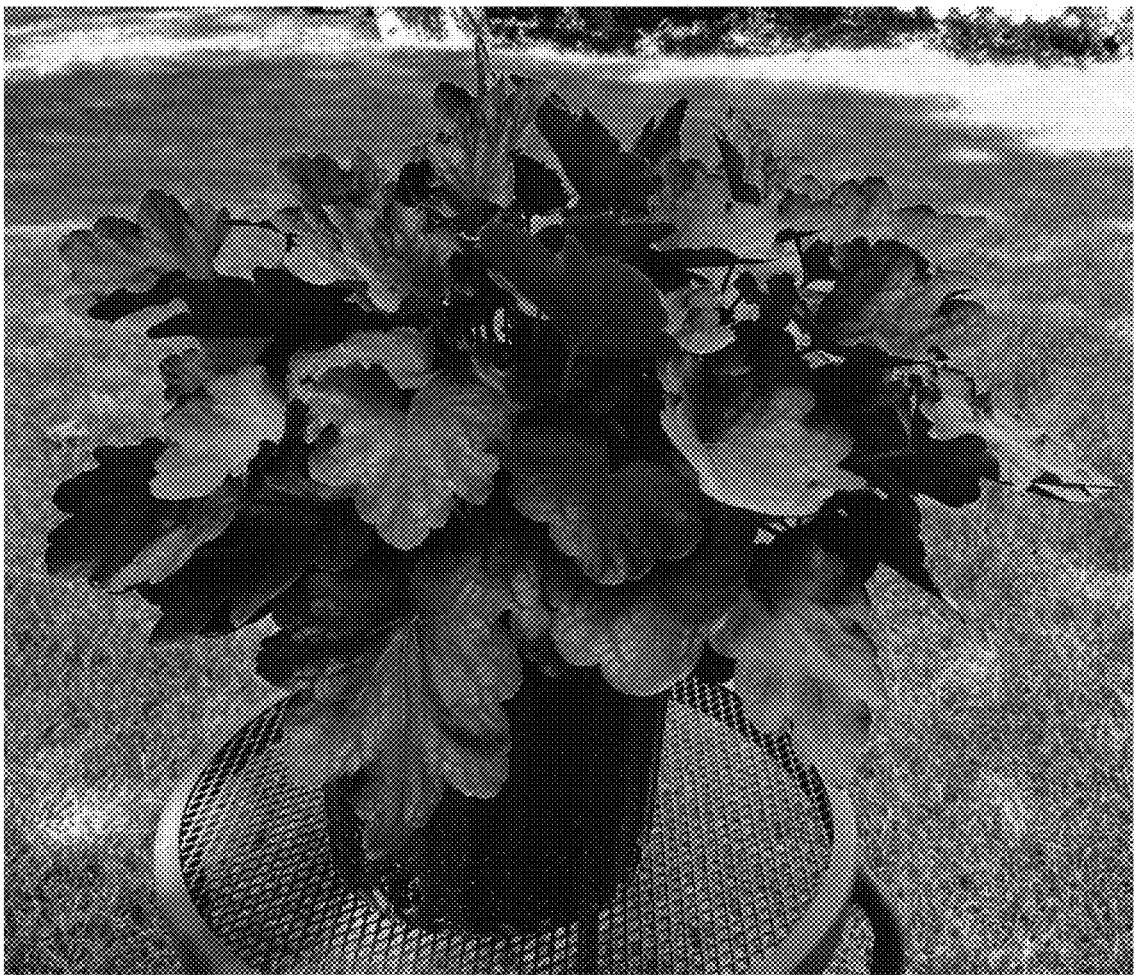
FIG. 1 illustrates a side view of the overall growth habit of 'Carnival Burgundy Blast'.
Figure 2:
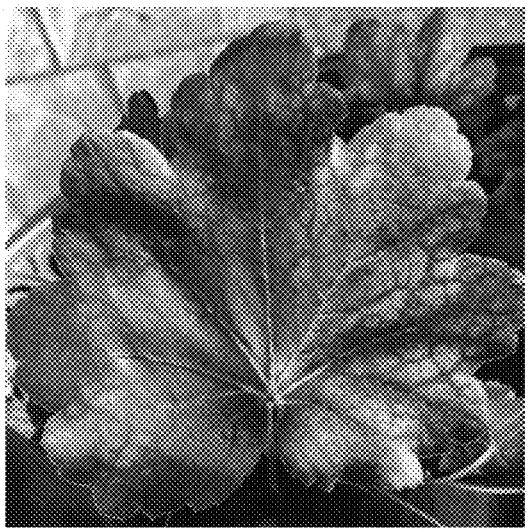
FIG. 2 illustrates a close-up view of an individual leaf of 'Carnival Burgundy Blast'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in August 2021 under natural light conditions in Naperville, Ill.

The following descriptions and measurements describe approximately nine-month-old plants produced from in vitro plantlets and grown under conditions comparable to those used in commercial practice. The plants were grown in 1.7-gallon containers for approximately 15 weeks in an outdoor shade nursery in West Chicago, Ill. Prior to transplant plants were grown in liners in a poly-covered greenhouse in West Chicago, Ill. Greenhouse temperatures ranged from an average high of 79.5° F. (26.4° C.) to an average low of 68.5° F. (20.3° C.), and supplemental lighting was provided daily for five hours during short days. Measurements and numerical values represent averages of typical plants.

Botanical classification: *Heuchera* x *hybrida* 'Carnival Burgundy Blast'.

Parentage:

*Female parent*.—'Carnival Black Olive', not patented.

*Male parent*.—Unknown.

Propagation:

*Type*.—In vitro propagation is preferred, divisions are possible.

*Time to initiate roots in vitro*.—Approximately 10 days at 20° C.

*Time to produce a rooted plantlet in summer*.—Approximately 42 days.

*Root description*.—Fine, fibrous.

*Rooting habit*.—Freely branching.

Plant description:

*Commercial crop time*.—Approximately 6 to 8 weeks from a rooted tissue culture plantlet to finish in a 10 cm container.

*Growth habit and general appearance*.—Clump-forming herbaceous perennial, mounded foliage.

*Growth rate*.—Moderately vigorous.

*Hardiness*.—USDA Zone 4a (−30° F. to −25° F./−34.4° C. to −31.7° C.).

*Size*.—Height from soil level to top of foliage: Approximately 22.0 cm. Width: Approximately 49.0 cm.

*Branching habit*.—No branching, basal rosettes of leaves on petioles. Number of rosettes per plant: Approximately 5.

Foliage description:

*General description*.—Moderately durable to environmental stresses. Quantity of leaves per rosette: Approximately 16. Fragrance: None. Form: Simple. Arrangement: Alternate to whorled. Density: Dense.

*Leaves*.—Aspect: Blade is at an acute angle to nearly perpendicular to petiole. Shape: Orbicular. Margin: Crenate with few and shallow indentations, moderately lobed, slightly wavy, ciliate. Apex: Minutely apiculate. Base: Cordate, sometimes slightly overlapping. Venation pattern: Palmate. Length of mature leaf: Approximately 11.2 cm. Width of mature leaf: Approximately 11.7 cm. Texture of upper surface: Dull, very weak rugosity, sparsely pubescent with short hairs. Texture of lower surface: Slightly glossy, sparsely pubescent with short hairs on venation. Color of upper surface of young foliage: Closest to 187A with an overlay of closest to N187D visible in areas between venation, base of main veins of 184A. Color of lower surface of young foliage: N186D. Color of upper surface of mature foliage: Closest to 187A with NN137A and with a faint overlay of closest to N187D visible in areas between venation, base of main veins of 184A and 146B; darkening in fall season to closest to N187A with NN137A and with an overlay of closest to N187C visible in areas between venation, base of main veins of 146C. Color of lower surface of mature foliage: Closest to N186D with 187A and with base of main veins of 147C; darkening in fall season to closest to N186C with 187A and with base of main veins lightening to 155A.

*Petiole*.—Length: Approximately 16.5 cm. Diameter: Approximately 3.0 mm. Texture: Sparsely pubescent. Color: 147C with an overlay of N186D, overlay is heavier on younger petioles.

*Stipules*.—Two leafy stipules located at the base of petioles. Apex: Acute. Length: Approximately 1.5 cm. Width: Approximately 3.0 mm. Color: Closest to N186D.

Flowering description: Flowers not observed throughout the growing season.

Seed and fruit production: Neither seed nor fruit production has been observed.

Disease and pest resistance: Resistance to pathogens and pests common to *Heuchera* has not been observed.

What is claimed is:

1. A new and distinct cultivar of *Heuchera* plant named 'Carnival Burgundy Blast', substantially as herein illustrated and described.

* * * * *